United States Patent [19]

Kahn

[11] Patent Number: 4,526,544

[45] Date of Patent: Jul. 2, 1985

[54] CYANOACRYLATE ROOT CANAL SEALER

[76] Inventor: Henry Kahn, 1724 Grand Bahama West, Palm Springs, Calif. 92262

[21] Appl. No.: 553,259

[22] Filed: Nov. 18, 1983

[51] Int. Cl.³ ............................................. A61C 5/02
[52] U.S. Cl. .................................... 433/224; 433/228; 523/117
[58] Field of Search .......................... 523/117; 433/224

[56] References Cited

U.S. PATENT DOCUMENTS

| | | | |
|---|---|---|---|
| 3,715,331 | 2/1973 | Molnar | 523/117 |
| 4,105,715 | 8/1978 | Gleave | 526/298 |
| 4,340,532 | 7/1982 | Lee, Jr. et al. | 433/224 |

FOREIGN PATENT DOCUMENTS 0050457  4/1982  European Pat. Off. ............ 523/117

OTHER PUBLICATIONS

*Dental Cosmos*–Jul. 26, "Filling the Root Canal", pp. 709–713 and 607, by Crane.

*Primary Examiner*—Paul R. Michl
*Assistant Examiner*—N. Sarofim
*Attorney, Agent, or Firm*—Eugene F. Friedman

[57] ABSTRACT

A method of sealing a tooth's root canal using cyanoacrylate solution. A tooth undergoing endodontic treatment must have the pulp tissue removed and the canal cleansed and shaped. It then receives a coating of a cyanoacrylate solution to its walls. When hardened, this solution seals the dentinal tubules lining the walls of the root canal and lateral canals, when present, thus preventing communication from the canal to the periodontal membrane. When the apical foramen remains small, it also may be sealed to prevent the passage of fluids and microorganisms to the adjacent area. Including a component which renders the cyanoacrylate solution opaque to X-rays will permit examination throughout the endodontic procedure. The sealing solution may include methyl, ethyl, isopropyl, isopropyl alpha, or normal-butyl cyanoacrylate of medical grade purity.

11 Claims, 3 Drawing Figures

U.S. Patent     Jul. 2, 1985     4,526,544
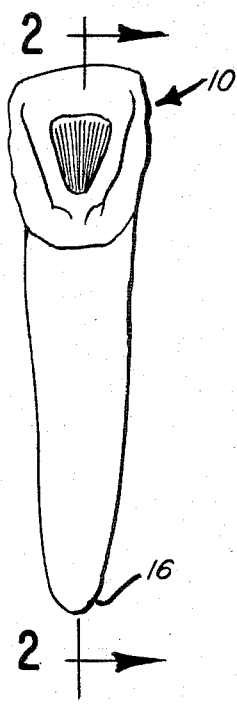
FIG. 1
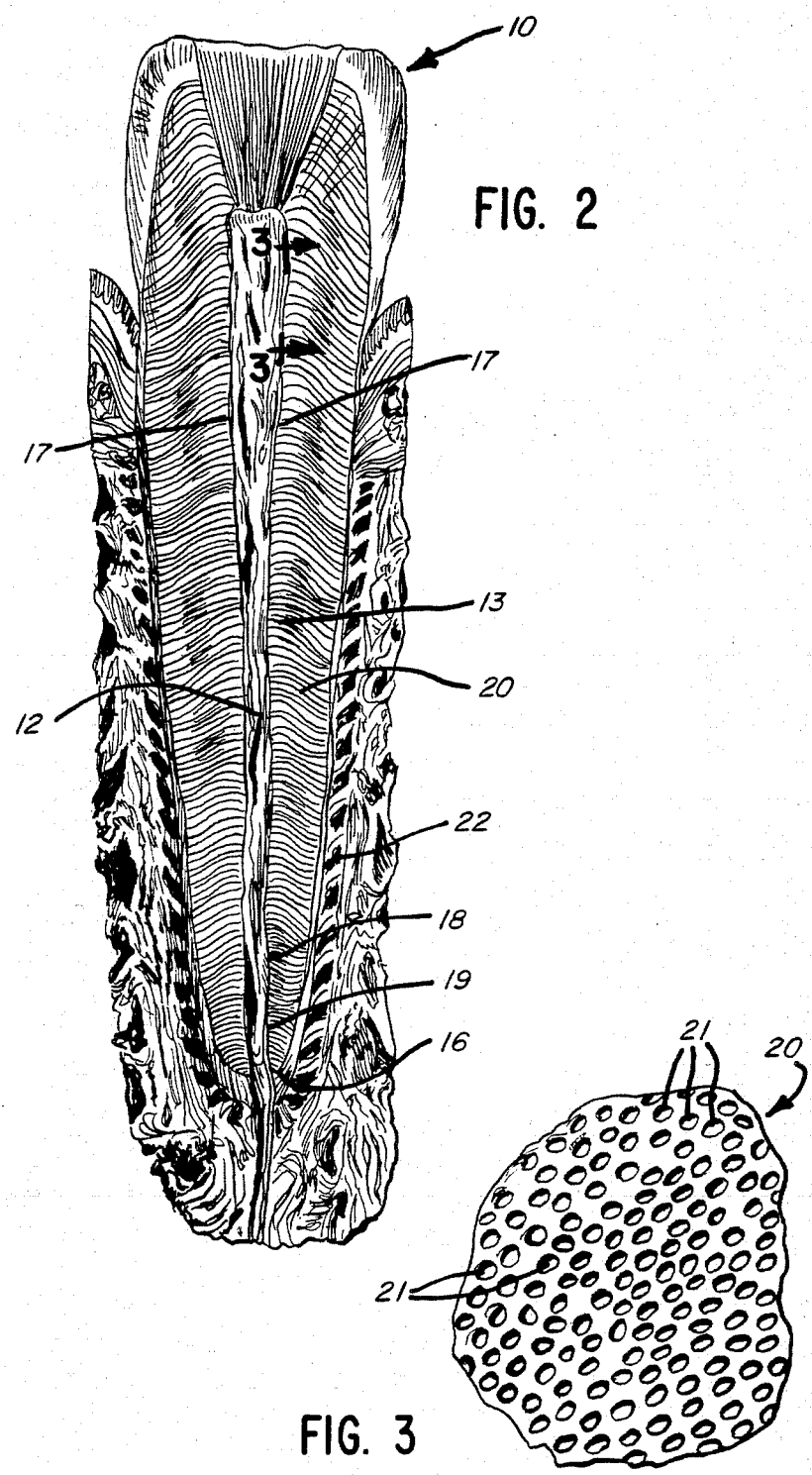
FIG. 2
FIG. 3

CYANOACRYLATE ROOT CANAL SEALER

BACKGROUND

Accepted endodontic practice typically includes several steps. Initially, a proper coronal access to the canal is obtained and, where possible, the patient relieved of pain. Next, the cleaning of the canal undergoes enlargement and tapering, and all debris and fluid removed from it. Lastly, for obturation, the tooth must be free of pain. The canal is then freshly irrigated, dried, and the root canal cement is applied. A master cone and accessory cones of gutta percha are laterally condensed to fill the canal. A permanent coronal restoration is then placed to finish the procedure.

Most failures in endodontics result from the incomplete sealing of the apical area, the porous dentinal tubules in the lateral walls of the canal, or both. There has been a constant effort to find an adequate material and method to improve the final seal and prevent the communication of substances from the root canal and its apex to the structure surrounding both.

The systematic study of different sealants has appeared in articles by P. M. Spradling et al., *Journal of Endodontics,* Vol. 8, 1982, pages 543 to 549 and D. Oerstavik, *International Endodontic Journal,* Vol. 16, 1983, pages 59 to 63. These articles indicate some inconsistency with other studies and between themselves as well as leaving doubt as to the most desired material.

Various glues formed from cyanoacrylates have undergone study in the oral environment. Y. Fukushi et al. examined it as a glue for resin restorations in *Journal of Dental Research,* Vol. 59(4), 1980, pages 662 to 699; M. J. Mitrosky, looked at cyanoacrylates as a bonding agent for the usual fillings as well as restorations in *Quintessence International,* Vol. 9, September, 1981, pages 871 to 874; and G. M. Brauer et al., *Journal of Dental Research,* Vol. 58, 1979, pages 1900 to 1907, looks at the use of cyanoacrylates to bond acrylic resins to dentine. These studies report varying results for cyanoacrylates as a bonding agent in the moist oral environment.

Many materials have found use as a sealer and as a filling material in endodontic therapy. However, none have obviated the desire for materials with improved sealing and bonding properties.

SUMMARY

Incorporating a liquid, medical-grade, bacteriostatic cyanoacrylate into endodontic therapy results in an improved sealer for root canals. The usual procedure involves the removal of the pulp and the enlargement of the root canal. Application of the cyanoacrylate solution upon the clean dentinal walls of the canal and to the apical opening at the tip of the canal provides an improved sealant.

An acrylate resin solution applied to the canal should seal it against the leakage of undesired material into that area. It should preferrably also seal the apical opening as well as the dentinal tubules. Cyanoacrylate solutions have shown the capability of hardening into an acceptable sealer. Cyanoacrylates can include methyl, ethyl, isopropyl, isobutyl alpha-, and normal-butyl cyanoacrylate of medical grade purity.

The resulting seal retards the leakage into the canal of tissue-fluids and bacteria that encourage the development of pathology. The cyanoacrylate also engenders a rapid setting of the sealer in the moist canal environmental.

In addition to sealing the canal walls and small apices, the solution, made into paste by the addition of opaque components, can fill the entire canal. It can thus represent an alternate to the time-consuming conventional method of obturating the canal using a hard core material, such as gutta percha.

Adding an X-ray opaque substance to the cyanoacrylate solution allows the dentist to monitor the entire procedure. This helps insure the control of the material whether in liquid or paste form.

BRIEF DESCRIPTION OF THE FIGURES

FIG. 1 gives an external, lingual elevational view of an entire lower central incisor removed from its surrounding tissue.

FIG. 2 provides a cross-sectional view along the line 2—2 of the tooth of FIG. 1 included in its usual supporting bone structure.

FIG. 3 shows an enlarged view along the line of 3—3 of FIG. 2 of the dentinal tubules opening into the root canal wall from the cementum layer.

DETAILED DESCRIPTION

Root canal therapy generally commences with the creation of an opening to the root canal such as on the lingual surface of the lower central incisor's crown 10, FIG. 1. The affected pulp 12, in FIG. 2, is then removed and any bleeding controlled. This is followed by the cleansing and shaping of the canal 13.

A series of graduated, tapered files are used along with constant irrigation to shape and cleanse the canal. The result is the removal of soft predentin found on the walls of the canal and a well flared canal free of debris and microorganisms. It also produces a definite seat preparation just short of the canal's apex. The above treatment of the canal 13 then permits the obturation of the canal.

Once cleansed, shaped, and dried the root canal 13 receives a coating of cyanoacrylate solution. The sealing solution then dries in the canal.

Applying the cyanoacrylate solution to the small apical seat, which should be short of the radiographic apex 18, creates a "plug" 19 at the apex 16 of the shaped root canal 13. This plug 19 thus seals the root canal 13 and prevents the leakage of tissue-fluids and microorganisms to and from the canal 13. In addition, the cyanoacrylate solution forms a necessary seal all along the total length of the walls 17 of the root canal 13 to th apical foramen 18. The canal can then undergo obturation with gutta percha in the usual accepted manner.

The dentin 20 surrounds the root canal 13. It consists of the dentinal tubules 21 as depicted in FIG. 3. These tubules 21 in the dentin extend the entire length of the root canal 13 and form its porous walls 17. The dentin extends laterally to the cementum 22.

The dentinal tubules 21 whose ends create the porous walls of the root canal 13 are sealed by the application of the cyanoacrylate solution. This prevents the leakage through the dentinal tubules 21 laterally to the periodontal membrane.

Completing the endodontic treatment requires the filling of the sealed root canal 13. One technique involves the use of cyanoacrylate in the form of a radioopaque paste. It may be applied to the root canal 13 as an alternative to the traditional hard core gutta percha filling material.

The paste includes the cyanoacrylate with a finely divided powder. The latter may take the form of the solid component Grossman's, Dr. Walk's, or Kerr's sealers, or even calcium hydroxide. All of these include a component opaque to X-rays. This allows the dentist to follow the course of treatment with the usual radiographic techniques. Adding sufficient powder will provide a paste of the desired consistency. Even in the form of a thick paste, the material still submits to application through a syringe. The powder used in the paste should include only very small particles. This allows the sealer and filler to enter the small tubules and crevices of the root canal.

The radioopaque paste may also prove useful in place of the usual amalgam for filling the apices at the tip of a root. An empty volume in the supporting bone tissue results from the removal of a large abscess or cyst at the tip of a root. During surgery, the tip of the root is cut and the pathological tissue in the canal, removed. The resulting empty space in the root canal may then be filled with the cyanoacrylate paste.

The cyanoacrylate paste may prove particularly desirable in the case of a child's damaged tooth. The tooth, not yet fully formed, displays open apices. The cyanoacrylate paste, in a thick form similar to the pastes presently used, is carefully applied into the canal with a syringe to seal the apices.

Typical cyanoacrylates that may find acceptable use in sealing root canals include methyl, ethyl, isopropyl, isobutyl alpha, and normal-butyl cyanoacrylate of medical grade purity. Adding a radio-opaque substance to the cyanoacrylate solution permits the endodontist to observe the position of the material in the canal by means of the radiograph.

An in vitro study compared the sealing ability of cyanoacrylate to other substances now in use for this purpose. These latter include gutta percha with Grossman's sealer; gutta percha with Hydron as a sealer; and gutta percha with $AH_{26}$. Gutta percha also was used with the cyanoacrylate used as the sealer. The tests for each of these sealants employed a group of ten extracted singe-root human teeth. An additional group of teeth were obturated with gutta percha having no sealer. As a control group, teeth prepared in the same fashion as above received a plugging at the apex with wax and no other obturation.

In the actual study, the 60 teeth underwent soaking in 5.25% NaOCl for one hour to remove any adherent tissue. Removing the crowns allowed the filing of the canals to about 2 mm. beyond the apex with graduated files up to size 50. The canals then underwent a flaring to a size 90 file. The teeth then received a rinsing and a drying with air prior to obturation.

After cleaning, the control group received a plug of wax at the apex. A further group of ten teeth received obturation only with a size 60 gutta percha master cone dipped in chloroform for three seconds. The fitting of the cone permitted it to slightly extend beyond the apex. Lateral condensation was accomplished with no sealer and medium fine gutta percha points.

The obturation of another group proceeded in the same manner but had Grossman's sealer placed in the canel prior to the gutta percha with a 45 file turning counter clockwise during its removal. The sealer also coated each medium fine point placed in the canal. The sealer and a portion of the gutta percha extended from the apex. The same procedure utilized $AH_{26}$ as the sealer on a different set of teeth.

The next group included Hydron (from NDP Dental Systems, Inc., New Brunswick, N.J.) as a sealer. The preparation of the Hydron proceeded through a quick mixing on a glass slab. A color change provided indication of its fast set. The treatment then proceeded as before.

A tuberculine syringe found use in placing the cyanoacrylate within the canals of the last group. The syringe expressed a small amount of the solution continuously during its removal from the canal. The master cone, after being dipped with chloroform, obtained a coating of cyanoacrylate as a sealer. The canal also received medium fine points of gutta percha in the condensation procedure. Exposure to air hastened the setting of the cyanoacrylate.

All of the teeth then received three coats of pink nail polish upon their entire root surfaces. Excess gutta percha extending beyond the apex on all of the teeth except those in the control group was cut off at the end of the root with a sharp scalpel.

The apices of all the teeth then remained submerged in methanlene blue dye for a week. After their removal, each of the groups of specimens were placed in a separate humidor.

Shaving of the root tips then permitted the determination of the length of the tooth penetrated by the dye. The control group showed no penetration except for one tooth where the dye penetrated 0.5 mm. from the tip. This minimal penetration may have resulted from an operator erroneously leaving a small uncovered orifice.

The gutta percha with no sealer permitted dye penetration of 4.0 to 8.0 mm. with a mean of 5.9 mm. The Grossman's sealer with the gutta percha had dye penetration of from 2.5 to 6.0 mm. with a mean of 5.9 mm. The $AH_{26}$ displayed a dye penetration of 0.0 to 3.5 mm. with a mean of 1.6 mm. The Hydron group permitted dye penetration of from 2.0 to 6.5 mm. and had a mean of 4.8 mm.

The cyanoacrylate group of teeth displayed dye penetration of from 0.5 to 1.0 mm. with a mean of 0.6 mm. These tests suggest that the cyanoacrylate solution may represent the superior sealing agent.

A more extensive investigation studied 120 single-rooted human maxillary and mandibular roots. All of the teeth, after extraction, were stored in 10 percent formalin. Radiography confirmed root canal patency and closure of the apex. Soaked in a 2.25 percent sodium hypochlorite solution for a week removed soft tissues from the root surfaces.

A high-speed #701 fissure bur removed the crowns at the cementoenamel junctions. Each canal was cleaned and shaped to the apical foramen to a size 50K file. The rest of each canal was flared by the step-back filing technique. After flaring, the patency of the apical opening was checked with a No. 50K file. The canals received an irrigating 2.25 percent solution of sodium hypochlorite during cleaning and shaping. Subsequently, the teeth were stored in distilled water.

Each of six groups randomly received 20 teeth. In the negative control group, the apical openings of the teeth were plugged with 1 to 2 mm. of wax without any root canal filling material. The coronal openings of these teeth were filled with 2 to 3 mm. of cavit. In the positive control group, the canals were filled with gutta percha without any root canal cement. The third, fourth, and fifth consisted of teeth whose canals were filled, respectively, with gutta percha and Hydron, AH-26 and Grossman sealer as root canal sealers by the lateral condensation technique. The gutta percha cones were fitted within 1 to 1.5 mm. of the apical opening of each root with good tugback. Each root canal received two coatings, with a No. 45K file applying the assigned sealer. The apical 2 to 3 mm. of the master gutta percha cone was dipped in chloroform for 1 to 2 sec. before entering the root canal. After the master gutta percha point, the remainder of the canal was filled with gutta percha using the lateral condensating technique.

In the sixth group, isopropyl cyanoacrylate was deposited into the root canals through a 30-guage needle. The canals were then filled with gutta percha in the same fashion as for the other groups.

Obturation was evaluated with buccolingual and mesiodistal radiographs. Canals incompletely filled were reobturated.

After obturation, 2 to 3 mm. of gutta percha were removed from the coronal opening of each canal with warm pluggers. Cavit then filled resulting space. Each tooth then entered a capped vial containing $2 \times 2$ in. guaze pads saturated with water. The sealer was allowed to set at room temperature for 48 hrs. After drying on guaze pads, the roots, except for the apical 2 mm., received two coats of nail polish.

The roots were then immersed in India ink for 24 hrs. Afterwards, placing them in acetone removed the nail polish and then in 20 percent formic acid at room temperature for 7 to 10 days effected decalcification. The roots becoming soft and the radiographs showing no calcified tissue indicated the completion of the decalcification. After the decalcification and a rinsing in running tap water overnight, the teeth underwent dehydration in an 85 percent ethyl alcohol solution and then received two one-hour rinses in a 100 percent solution. Placing the roots in methyl salicylate from two to three hours rendered them transparent.

A millimeter ruler using a dissecting microscope measured the amount of leakage of the ink from the apical opening into the canal. An analysis of variance (ANOVA) tested for the statistical differences among the groups. Further, a q test determined the degree of significance of differences between all possible pairs of means among all the groups.

The mean values and standard deviations of the measurements of the extent of leakage in all groups appear in Table 1. The ink penetrated through the apical openings of only two roots in the wax plugged control group, and in all 20 teeth in the roots without any sealer. Among the experimental groups, canals sealed with the isopropyl cyanoacrylate allowed the least amount of leakage, followed distantly by those sealed with Hydron, AH-26, and Grossman root sealers.

One-way ANOVA showed statistical differences between the means of the groups. The q test showed that the mean of the cyanoacrylate group did not differ significantly from that of the wax-plugged control group. However, the means of all other groups differed significantly from that of the wax-filled control group and that of the canals filled with gutta percha and cyanoacrylates as a root canal sealer as seen in Table 2.

TABLE 1

Frequency and Extent of Apical Leakage in Canals, by Experimental Group

| Group | No. Teeth With Leakage (N = 20) | Average Leakage (mm.) | Standard Deviation |
|---|---|---|---|
| 1. Wax Plugged Roots | 2 | 0.05 | 0.15 |
| 2. Canals With Gutta Percha and Without Sealer | 20 | 6.65 | 3.09 |
| 3. Canals With Gutta Percha and Hydron | 20 | 5.05 | 2.53 |
| 4. Canals With Gutta Percha and AH-26 | 19 | 2.47 | 1.57 |
| 5. Canals With Gutta Percha and Grossman Sealer | 20 | 3.12 | 1.43 |
| 6. Canals With Gutta Percha and Cyanoacrylate | 6 | 0.57 | 1.36 |

The results from the wax-plugged control group showed that two coats of nail polish prevented India ink from penetrating into the root canals. The absence of a significant amount of leakage in this group indicated that penetration of ink into the root canals in other groups occurred through the apical openings. Of the experimental groups, the isopropyl cyanoacrylate appeared to provide a more reliable seal of the apical openings than the other sealers studied.

TABLE 2

Statistical Significance of Differences Between the Mean Values of Leakage of All Pairs of Groups

| Not Significant | 95% Significant (p 0.05) | 99% Significant (p 0.01) |
|---|---|---|
| 1 vs 6 | 2 vs 4 and 5 | 6 vs 2, 3 and 5 |
| 4 vs 5 | 3 vs 4 and 5 | 1 vs 2, 3, 4 and 5 |
| 2 vs 3 | 4 vs 6 | |

Accordingly, what is claimed is:

1. A method of endodontically treating a tooth comprising:
   (A) removing tissue from the root canal;
   (B) shaping said root canal; and
   (C) sealing the surfaces of said root canal with an cyanoacrylate resin solution.
2. The method of claim 1 wherein said acrylate resin solution includes a cyanoacrylate.
3. The method of claim 2 wherein said solution fills said canal.
4. The method of claim 3 wherein said cyanoacrylate is methyl cyanoacrylate, ethyl cyanoacrylate, isopropyl cyanoacrylate, isobutyl alpha-cyanoacrylate, or normal-butyl cyanoacrylate of medical grade purity.
5. The method of claim 4 wherein said solution is at least partially opaque to X-rays.
6. The method of claim 3 wherein at least a portion of said solution is placed in said canal in the form of a paste.
7. The method of claim 6 wherein said paste includes said cyanoacrylate resin and Ca(OH)$_2$.
8. The method of claim 6 wherein said paste includes said cyanoacrylate resin and the solid component of Grossman's, Dr. Walk's, or Kerr's sealer.
9. The method of claim 2 wherein said solution forms a plug at the apical opening of said tooth.
10. The method of claim 9 wherein said cyanoacrylate is methyl cyanoacrylate, ethyl cyanoacrylate, isopropyl cyanoacrylate, isobutyl alpha-cyanoacrylate, or normal-butyl cyanoacrylate of medical grade purity.
11. The method of claim 10 wherein said solution is at least partially opaque to X-rays.

* * * * *